US005321046A

United States Patent [19]

Sit et al.

[11] Patent Number: 5,321,046
[45] Date of Patent: Jun. 14, 1994

[54] HYPOCHOLESTEROLEMIC UNSYMMETRICAL DITHIOL KETALS

[75] Inventors: Sing-Yuen Sit, Meriden; John J. Wright, North Guilford, both of Conn.; Jeff A. Field, Burlington, Vt.

[73] Assignee: Bristol-Myers Squibb Company, New York, N.Y.

[21] Appl. No.: 970,594

[22] Filed: Oct. 27, 1992

Related U.S. Application Data

[63] Continuation of Ser. No. 583,616, Sep. 14, 1990, abandoned.

[51] Int. Cl.$^5$ .............. A61K 31/275; A61K 31/235; A61K 31/24; A61K 31/10; C07C 321/30; C07C 255/50; C07C 255/51; C07C 235/84

[52] U.S. Cl. .................. 514/522; 514/524; 514/525; 514/532; 514/533; 514/538; 514/616; 514/618; 514/713; 558/411; 558/416; 558/423; 558/425; 560/17; 562/431; 564/153; 564/154; 564/162; 568/38; 568/41; 568/46; 568/56; 568/57

[58] Field of Search ............. 562/431; 514/532, 616, 514/618, 713, 522, 525, 533, 524, 538; 560/17; 568/38, 41, 46, 56, 57; 564/153, 154, 162; 558/411, 416, 423, 425

[56] References Cited

U.S. PATENT DOCUMENTS 4,461,911  7/1984  Schutze et al. ............ 562/427
4,755,524  7/1988  Mueller et al. ............ 560/17 X Primary Examiner—José G. Dees
Assistant Examiner—Vera C. Clarke
Attorney, Agent, or Firm—Prabodh I. Almaula

[57] ABSTRACT

Disclosed herein are novel unsymmetrical dithiol ketals which are useful in the treatment or prevention of hypercholesterolemia, hyperlipoproteinemia, and atherosclerosis.

7 Claims, 4 Drawing Sheets

FIG.1

MINOR SIDE PRODUCT

3

TWO COMPOUNDS WERE MADE BY THIS APPROACH

$R_2 = R_5 = -C(CH_3)_3$,     $R_3 = R_6 = H$ $R_2 = R_5 = -CH_3$,     $R_3 = R_6 = H$

FIG.2 m = 1 AND 2

MINOR SIDE PRODUCT

HYPOCHOLESTEROLEMIC UNSYMMETRICAL DITHIOL KETALS

This application is a continuation of application Ser. No. 07/583,616, filed Sep. 14, 1990, now abandoned.

BACKGROUND OF THE INVENTION

1. Field Of The Invention

The present invention relates to unsymmetrical dithiol ketals composed of a farnesyl mercaptan unit and a thiol phenol moiety. The compounds of the present invention are useful in the treatment or prevention of hypercholesterolemia, hyperlipoproteinemia and atherosclerosis.

2. Description of the Prior Art

Unsymmetrical dithiol ketals composed of a farnesyl mercaptan unit and a thiol phenol moiety are unknown in the literature. However, examples of similar symmetrical diaryl dithiol ketals are abundant. (Newworth and Laufer, J. Med. Chem, 170, 13(4), 722).

An example of a known symmetrical diaryl dithiol ketal is Probucol (4,4'-(isopropyledevedithio)bis(2,6-ditertbutylphenol). Probucol is a potent synthetic hypolipidemic agent effective in human at dosage around 500 mg b.i.d. The mechanism of action of this symmetrical diaryl dithiol ketal has been a subject of debate for many years. It has recently been suggested that the antioxidation properties of Probucol is responsible for its therapeutic actions. (Minakami et. al., *Drug Res.* 1989, 39(II), 1090). Dithiol ketals are hydrolysed to give reductive intermediates which are capable of neutralizing any harmful oxidative products such as hydroxyl radical. The precise mechanism of how the reductive species are released is still unclear as is the interaction with the oxidizing toxic substances. Being a highly lipophilic compound, Probucol (or any other non-polar substance) is transported into plasma in lipoproteins, primarily in LDL and VLDL (Marshall, F. N., *Artery*, 1982, 10, 7), and is preferentially distributed in high concentrations in cell membranes which consist of phospholipids. Thus, it is strategically positioned to offer maximum protective action against oxidative modifications to the lipoproteins and cell membranes.

The unsymmetrical dithiol ketals of the present invention act not only as antioxidants, but also as potential biofeedback regulators. The unsymmetrical dithiol ketals of the present invention are also capable of down regulating the crucial hydroxymethylglutaryl coenzyme A reductase (HMGCo-A reductase) and, therefore, are more desirable for the treatment of hypolipidemia.

SUMMARY OF THE INVENTION

The generic structure of the present invention is represented by Formula (I)

FORMULA I wherein $R^1$ represents $C_1$ to $C_6$ alkyl, hydroxy, hydrogen, or a halide;

$R^2$, $R^3$, $R^4$, and $R^5$ are identical or different and independently of one another are each hydrogen, $C_1$ to $C_6$ alkyl, phenyl rings, or electron withdrawing groups such as carboxylic acid esters, amides, or nitriles;

$R^6$, and $R^7$ identical or different and independently of one another are each hydrogen, $C_1$ to $C_6$ alkyl, $C_1$ to $C_7$ cyclic alkyls, chloroalkyls, fluoroalkyls, or substituted carboxylic acids m is 0-2 n is 1-3.

When $R^1$ is hydroxy, the present invention prodrug esters of the compounds of Formula I, having the general structural Formula (II)

FORMULA II wherein $R^1$ represents a physiologically hydrolyzable ester, preferably an ester of nicotinic acid, succinic acid, or acetic acid; and $R^2$, $R^3$, $R^4$, $R^5$ $R^6$, $R^7$, m, and n are as described in Formula I.

The present invention also provides a process for the preparation of compounds of Formulas I and II.

The present invention further provides pharmaceutical compositions comprising at least one compound of Formula I or Formula II, or a salt, hydrate or solvate thereof, in combination with a pharmaceutical carrier or diluent.

The present invention also provides a procedure for the synthesis of the intermediates, 4-hydroxy-thiophenol, 2,6-dimethyl-4-mercaptophenol, 2,3-dimethyl-4-mercaptophenol, 2,5-dimethyl-4-mercaptophenol, 2-methyl-4-mercaptophenol, and 3-methyl-4-mercaptophenol.

The compounds of the present invention are useful in the treatment or prevention of hypercholesterolemia, hyperlipoproteinemia and atherosclerosis.

DETAILED DESCRIPTION OF THE INVENTION

The present invention provides novel unsymmetrical dithiol ketal compounds which are potent cholesterol suppressors in vitro and in vivo assays. They are useful in the treatment or prevention of hypercholesterolemia, hyperlipoproteinemia and atherosclerosis. The present invention also discloses an efficient preparative procedure for the synthesis of the crucial intermediates.

The generic structure of the present invention is represented by Formula (I)

FORMULA I wherein $R^1$ represents $C_1$ to $C_6$ alkyl, hydroxy, hydrogen, or a halide;

$R^2$, $R^3$, $R^4$, and $R^5$ are identical or different and independently of one another are each hydrogen, $C_1$ to $C_6$ alkyl, phenyl rings, or electron withdrawing functional groups such as carboxylic acid esters, amides, or nitriles;

$R^6$, and $R^7$ are identical or different and independently of one another are each hydrogen, $C_1$ to $C_6$ alkyl, $C_1$ to $C_7$ cyclic alkyls, chloroalkyls, fluoroalkyls, or substituted carboxylic acids;

m is 0-2; and n is 1-3.

When $R^1$ is hydroxy, the present invention also provides prodrug esters of the compounds of Formula I, having the general structural Formula (II)

FORMULA II wherein $R^1$ represents an ester, preferably an ester of nicotinic acid, succinic acid, or acetic acid; and $R^2$, $R^3$, $R^4$, $R^5$ $R^6$, $R^7$, m, and n are as described in Formula I.

The term $C_1$ to $C_6$ alkyl as used herein and in the claims (unless the context indicates otherwise) means saturated or unsaturated, branched or straight chain alkyl groups such as methyl, ethyl, propyl, isopropyl, butyl, isobutyl, t-butyl, etc. Unless otherwise specified in the particular instance, the term "halogen" as used herein and in the claims is intended to include chlorine, fluorine, bromine and iodine.

The term prodrug, as used herein and in the claims (unless the context indicates otherwise) denotes an analog of an active drug which after administration is capable of undergoing hydrolysis of the ester moiety or oxidative cleavage of the ester moiety so as to release active free drug. The physiologically hydrolyzable esters serve as prodrugs by being hydrolyzed in the body to yield the parent drug per se.

The compounds of the present invention are generally prepared by combining a suitable thiophenol and farnesyl mercaptan unit in the presence of 2,2'-dimethoxypropane or the dimethoxyketal of a suitable ketone component and the reaction is catalyzed by borontrifluoride etherate.

Figure 1:
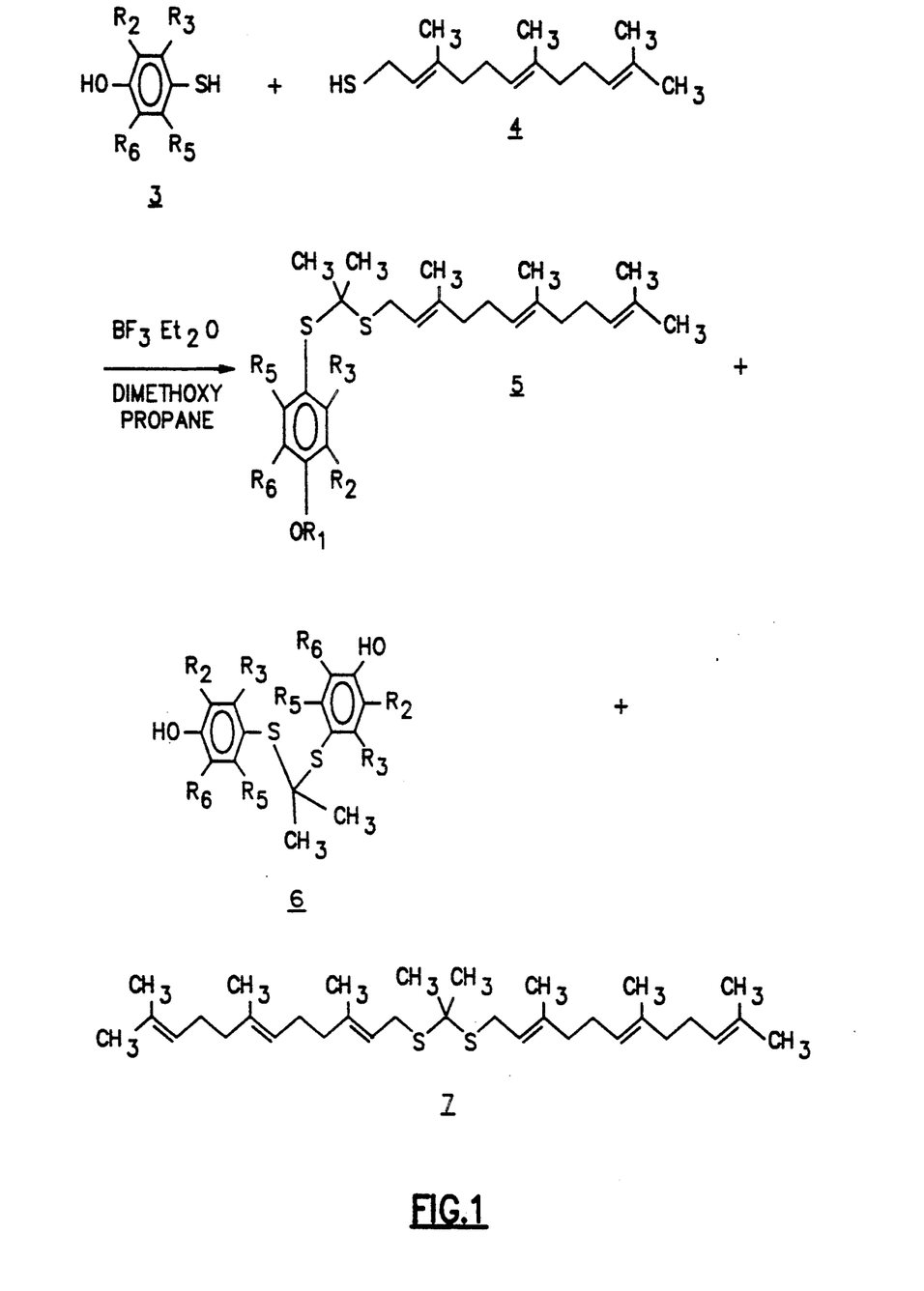
FIG. 1 shows the schematic preparation of the compounds of the present invention.

Statistically, three products are expected to be formed but in reality, the desired product is always formed in major proportion. The side products from this reaction are generally removed by filtration and silica gel chromatography. A schematic preparation of the compounds of the present invention is shown in FIG. 1.

Figure 2:
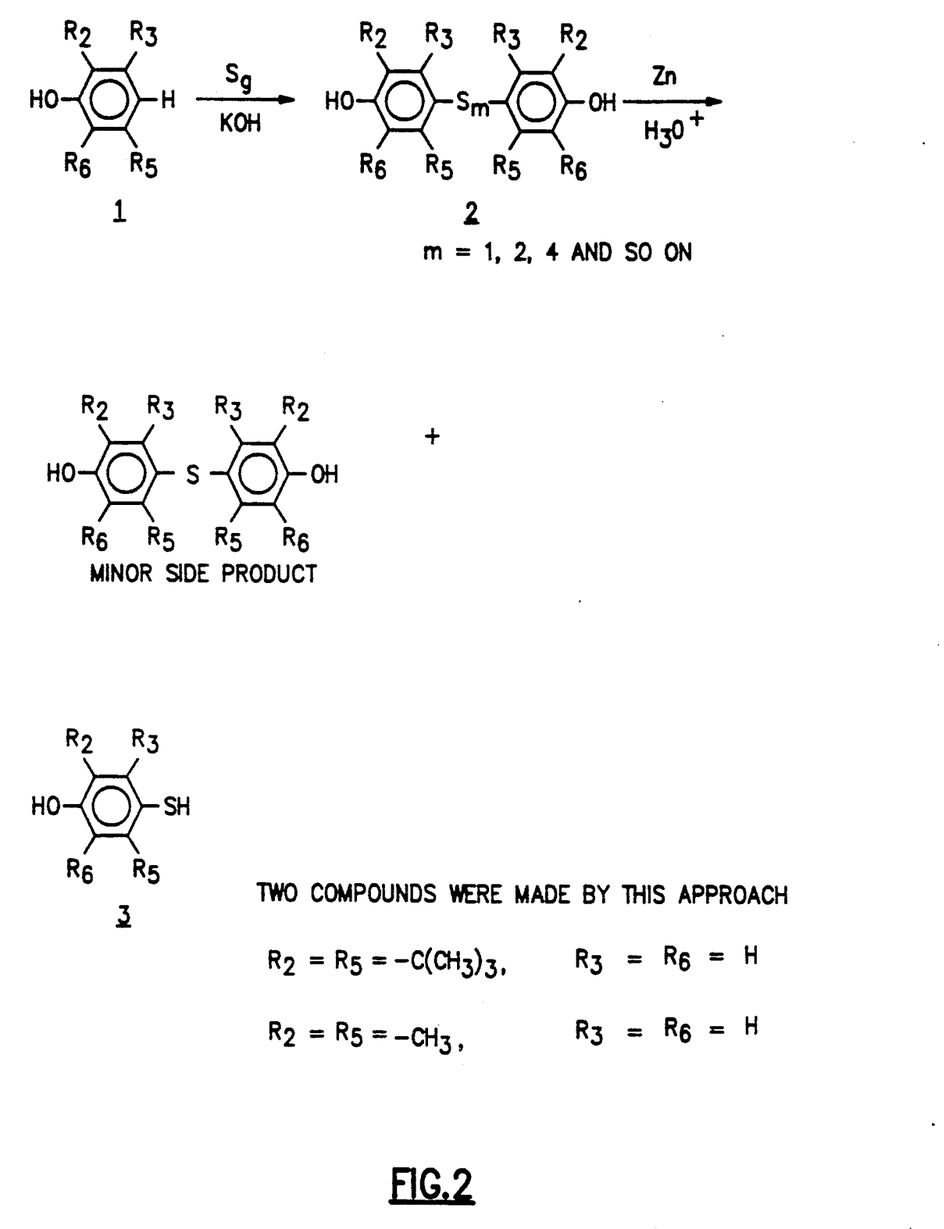
FIG. 2 shows a general procedure for the preparation of arylthiols.
Figure 3:
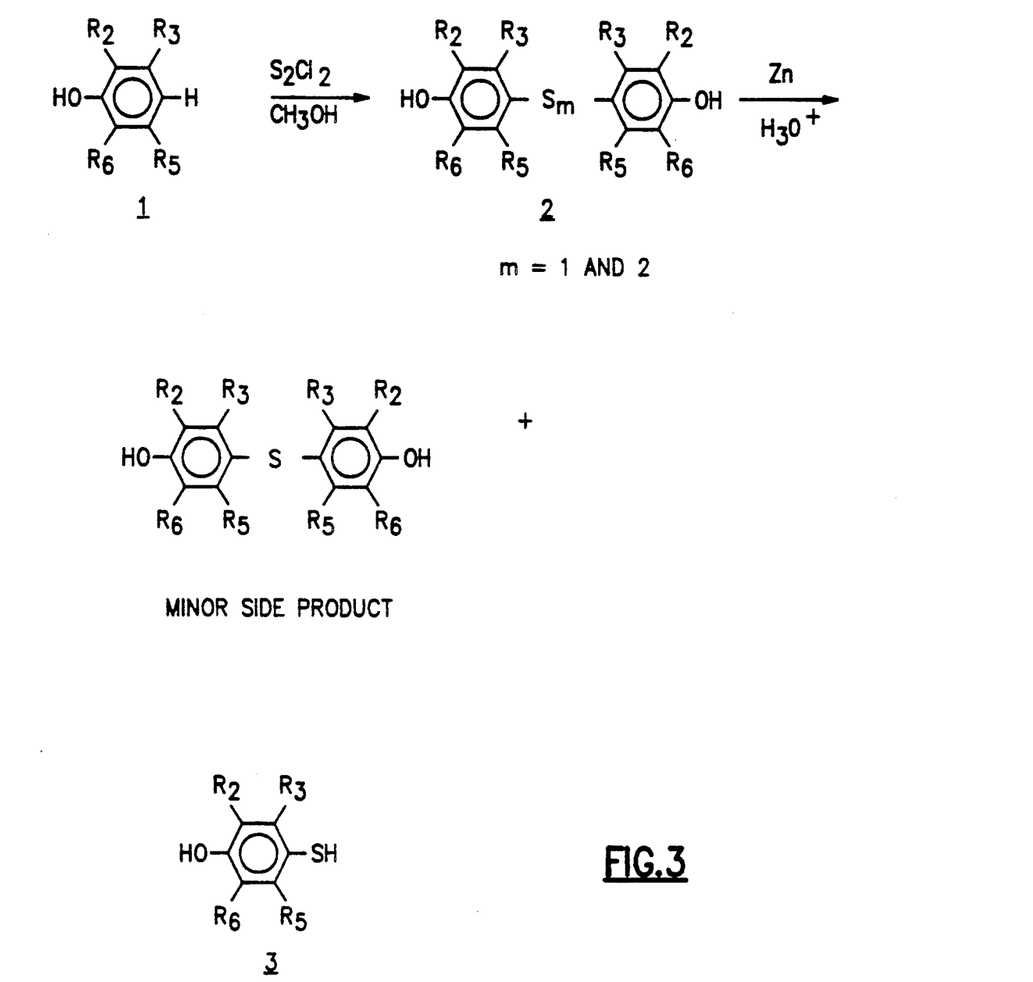
FIG. 3 shows a general procedure for the preparation of arylthiols.

The arylthiols employed in this synthesis ar not all commercially available. A general procedure of preparation is shown in FIG. 2 and FIG. 3.

The procedure used here called for adding sulfur chloride into a methanolic solution of the substituted phenols. Two products were formed, the desired product was finally obtained by a zinc metal reduction in mineral acids such as HCl. The use of methanol was necessary because the condition effectively attenuated the chemical reactivity of sulfur chloride (a potent electrophile) capable of inducing multiple sulfuration.

The 4-mercaptophenols prepared by this method were generally purified by crystallization from mixtures of hexanes and ethyl acetate. Those oily 4-mercaptophenols (such as entries 6, 7, 8, Table 1) were purified by silica gel column chromatography eluted with mixtures of hexanes and ethyl acetate. The purified materials are stable solids or liquids and are reasonably stable under normal atmospheric conditions for a short period of time. These intermediates were normally used for the next step right away or were stored under nitrogen at $-20°$ C. if not used immediately.

Previous literature procedure is available for the same transformation, but the present method offers several advantages including:

(a) Cleaner transformation;

(b) Better overall yield; and (c) Less obnoxious side products during the zinc metal reduction stage.

TABLE 1

Summary of Physical Properties

| No. | $R_2$ | $R_3$ | $R_4$ | $R_5$ | M.P. |
|---|---|---|---|---|---|
| 1[1] | $CH_3$ | | $CH_3$ | H | H | 98–99° C. |
| 2[1] | $CH_3$ | | H | $CH_3$ | H | 85–86° C. |
| 3[1] | | $(CH_2)_4$ | | H | H | 71.5–72.1° C. |
| 4[1] | $CH_3$ | | H | H | H | 38–39° C. |
| 5[1] | H | | $CH_3$ | H | H | 45–49° C. |
| 6[1] | $C(CH_3)_3$ | | H | H | H | OILY |
| 7[1] | $CH(CH_3)C_2H_5$ | | H | H | H | OILY |
| 8[1] | $C_6H_5$ | | H | H | H | OILY |
| 9[2] | $CH_3$ | | H | H | $CH_3$ | 82–83° C. |
| 10[3] | $C(CH_3)_3$ | | H | H | $C(CH_3)_3$ | |

[1]Prepared by the improved procedure
[2]Prepared by the original sulfur procedure and the improved procedure.
[3]Purchased from commercial sources, it was also synthesized by the original procedure.

Biological Activity (a) Isolated Hepatocyte cholesterol biosynthesis assay: HepG2 Cell Culture Model—14C-Acetate Incorporation Assay HepG2 cells obtained from the American Type Culture Collection were routinely passed in RPMI-1640 plus 10% fetal bovine serum (FBS) and were subculture into 35 mm diameter wells for experiments. At approximately 60–70% confluence, the medium was changed to 2.0 ml RPMI-1640 plus 7% lipid-depleted serum (LDS) to induce cholesterogenesis as suggested by Burki et al., *J. Lipid Res.*, 28: 1199–1205, (1987). The LDS medium supplement was prepared according to Cham et al., *J. Lipid Res.*, 17: 176-181, (1976). After about 16 hours in LDS containing media, test compounds were added in dimethylsulfoxide vehicle (0.5% v/v final conc.) for the period of time indicated in the data (generally 4 hours). Cholesterol synthesis was then directly determined by the incorporation of 2-14C-acetate (1.8-3.0 mCi/mmol) into digitonin-precipitable sterols essentially as described for the rat hepatocyte method above. Greater than 97% of the radiolabelled sterol isolated by this procedure was cholesterol as judged by HPLC. Percent inhibition was calculated from the average of duplicates or triplicates vs. controls receiving vehicle.

(b) LDL Oxidation Assay

The LDL oxidation assay was done as described by Leake et. al., *Proc. Natl. Acad. Sci. USA*, 1984, 81, 3883. Vascular endothelial (or fibroblast) cultures were passed into 6 well (35 mm in diameter) plates. When the cells achieved approximately 85% confluency, they were washed and 1 ml of F-10 culture medium containing 100 ug protein of human low-density lipoprotein is added. After about 24 hours at 37° C. in a humidified atmosphere (5% $CO_2$), the media was removed and assayed for thiobarbituric acid reactive substance (TBARS). Controls were included with each assay. Maximal oxidation of LDL values were obtained from cells to which the only vehicle added was DMSO, 0.1%, while baseline oxidation values were obtained from parallel cell-free wells. Also included in each experiment is the standard antioxidant, probucol. After baseline oxidation was subtracted, percent inhibition for an experimental compound was computed as shown below.

$$\frac{\text{Maximal oxidation} - \text{oxidation in presence of compound}}{\text{maximal oxidation}} \times 100 = \% \text{ INHIBITION}$$

In general, in the in vitro screen, the free phenolic compounds ($R^1$=OH, FIG. 1) were more active in suppressing cholesterol biosynthesis than the corresponding compounds without an acidic proton.

| Compound of Example | HepG2 @ 10 μM |
|---|---|
| 15 | 75% |
| 36 | 20% |

It is believed that the free phenolic functionality is, at least, partly involved in the cholesterol suppression mechanism.

The cholesterol suppression potency is further augmented by introducing electron withdrawing group at the dithioketal carbon atom.

| Compound of Example | HepG2 @ 10 μM |
|---|---|
| 11 | 63% |
| 27 | 79% |

The increase in suppression potency may be attributed to the enhanced chemical stability toward hydrolysis thereby allowing more active drug to reach the site of action.

More importantly, the compound of Example 27 was shown to down-regulate the key enzyme in the cholesterol biosynthesis, i.e. hydroxymethylglutaryl coenzyme A reductase (HMGcoA reductase). The mechanism of action is probably by down regulating the HMGCoA reductase activity level through a biofeedback mechanism.

| biosynthesis Compound of Example | HEPG2 Sterol reductase inhibition @ 10 μM | HMGCo-A suppression @ 10 μM |
|---|---|---|
| 11 | 63% | 37% |
| 27 | 79% | 51% |

(c) In vivo cholesterol biosynthesis in hamsters was assayed using the following protocol: four groups of hamsters (male $F_1$ B, fed 0.5% cholesterol 10% coconut oil), average weight 120-150 gm, were run in parallel (N=10 per group). The animals were initially fed the atherogenic diet for 20 days to determine their pre-drug plasma lipid levels. They were randomized so that each group had the same average plasma total cholesterol. The three of the four groups were started on their respective drug containing diet (day 0), while the remaining group served as controls.

Twenty days after drug treatment, plasma lipids were assayed and the results are summarized in Table 3.

TABLE 3

| Summary of Plasma Lipids Levels | | |
|---|---|---|
| | Day 0 | Day 21 |
| | | Total cholesterol mg/dl |
| Control | 389 ± 67 | 407 ± 144 |
| Compound of Example 11 | 399 ± 82 | 336 ± 90 |
| | | LDL Cholesterol mg/dl |
| Control | 305 ± 71 | 333 ± 137* |
| Compound of Example II | 319 ± 89 | 256 ± 85 |

*$P < 0.05$ Compound to day 0 bleed of the same group (paired T test).

The in vivo screen of Example 11 in $F_1B$ hamsters indicated a significant reduction in LDL-cholesterol (−25% over control) and overall cholesterol (−18% over control). The ability of this series of dithiol ketals in suppressing cholesterol, in particular, LDL-cholesterol represents a novel finding of chemotherapeutic agents in treating hypercholesterolemia.

According to the present invention, therefore, there is provided a method for therapeutically treating a mammalian host with at least one compound of Formula I or Formula II, which may be administered in free base form, or in pharmaceutically acceptable salt form, e.g. suitable acid addition salts and quaternary ammonium salts.

In another embodiment, this invention relates to a method of inhibiting cholesterol biosynthesis in a mammal in need thereof, which comprises administering to said mammal an effective cholesterol inhibitory dose of at least one compound of Formula I or Formula II.

Another embodiment this invention relates to the procedure for preparing the compounds of Formulas I and II.

In another embodiment, this invention relates to a a preparative procedure for the synthesis of the intermediates 4-hydroxy-thio-phenol, 2,6-dimethyl-4-mercaptophenol, 2,3-dimethyl-4-mercaptophenol, 2,5-dimethyl-4-mercaptophenol, 2-methyl-4-mercaptophenol, and 3-methyl-4-mercaptophenol.

In yet another embodiment, this invention relates to pharmaceutical compositions comprising at least one compound of Formula I or Formula II, or a salt, hydrate or solvate thereof, in combination with a pharmaceutical carrier or diluent.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents, and the like. The tablet may, if desired, be film coated by conventional techniques. If a liquid carrier is employed the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and the like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active component, that is, the compound of Formula I or Formula II according to the invention.

It will be appreciated that the actual preferred dosages of the compounds of the present invention will depend not only on such factors as the weight of the patient and mode of administration, but also on the degree of cholesterol biosynthesis inhibition desired, and the potency of the particular compound being utilized. The decision as to the particular dosage to be employed (and the number of times to be administered per day) is within the discretion of the physician, and may be varied by titration of the dosage to the particular circumstances of this invention for the satisfactory inhibition or reduction of cholesterol biosynthesis, each oral dosage unit will contain the active ingredient in an amount of form about 0.3 mg/kg to about 30 mg/kg body weight, and most preferably from about 0.1 mg/kg to about 10 mg/kg body weight. The active ingredient will preferably be administered in equal doses from one to four times a day. However, usually a small dosage is administered, and the dosage is gradually increased until the optimal dosage for the host under treatment is determined.

The present invention is illustrated by the following examples which are not intended to be construed as limiting the scope of the invention. All temperatures are understood to be in degrees in C when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlets (br.s), singlets (s), multiplet (m), doublet (d), doublet of doublets (dd), triplet (t), or quartet (q). The infrared (IR) spectral descriptions include only absorption wave numbers (cm$^{-1}$) having functional group identification value. The IR determinations were employed using potassium bromide (KBr). All compounds gave satisfactory elemental analyses.

EXAMPLE 1

General Procedure: Step 1—Preparation of 2,3-Dimethyl-4-mercaptophenol

To a solution of 2,3-dimethylphenol (10 g, 81.9 mmoles) in anhydrous reagent grade methanol (200 mL) at room temperature was added dropwise sulfur monochloride (4 mL, d=1.688 8/ mL, 135.03 g/mol, 50.0 mmoles). The reaction was mildly exothermic and the color became somewhat darker. The mixture was stirred at room temperature for about one hour and was examined by analytical thin layer chromatography eluted with 20% ethyl acetate in hexanes (v/v). TLC showed no starting material and the formation of two other spots was evident. The crude mixture was evaporated to one half of the original volume and was diluted with 200 ml of diethylether and 100 ml of distilled water. The heterogeneous mixture was subjected to the next reduction step without further purification.

The heterogeneous sulfuration mixture was treated with granular zinc metal (20 g, excess) and 100 ml of conc. hydrochloric acid at room temperature for about 16 hours. When the reduction was complete (monitored by TLC), the organic layer was separated, washed with water to remove as much zinc residue as possible. The organic layers were combined, concentrated and the crude product was preabsorbed on 40 g of fine silica gel (type-H). The desired product was purified by silica gel column chromatography eluted with 5% ethyl acetate in hexanes (v/v), 5.5 g of the title compound was isolated (36 mmoles, 44%). The product could be further purified by crystallization from ethyl acetate and hexanes.

m.p.=98°–99° C.;

MS (CI): m/e=155 for (M+H)$^+$;

IR (KBr) $\nu_{max}$: 3316 (br), 1454 (s), 1426 (s), 1274 (s), 1184 (s), 1066 (s), 796 (s) cm$^{-1}$;

$^1$H NMR (CDCl$_3$) $\delta$: 7.06 (1H, d, J=8.3 Hz), 6.52 (1H, d, J=8.3 Hz), 4.54 (1H, s), 3.12 (1H, s), 2.29 (3H, s), 2.15 (3H, s);

$^{13}$C NMR (CDCl$_3$) $\delta$: 152.4, 137.7, 129.5, 123.8, 120.8, 113.2, 18.0, 12.4;

Anal. Calcd. for C$_8$H$_{10}$SO: C, 62.30; H, 6.54. Found: C, 64.00; H, 6.76.

EXAMPLE 2

General Procedure: Step 2—Preparation of 2,6-Dimethyl-4[[1-methyl-1-[(3,7,11-trimethyl-2,6,10-dodecatrienyl)thio]ethyl]thio]phenol A catalytic amount of boron trifluoride etherate (10.54 mL) was added to a chilled solution (ice bath) of farnesyl mercaptan (8.0 g, 33.6 mmoles), prepared according to the procedure published by U.S. Pat. No. 3,665,040, 3,5-dimethyl-4-hydroxy thiophenol (4.33 g, 28.0 mmoles) and 2,2-dimethoxy propane (4.1 mL, 33.6 mmoles) in 200 mL of reagent grade benzene. The slightly cloudy solution was stirred at 0° C. for approximately 15 minutes before the ice cooling bath was removed and the mixture was allowed to warm to ambient temperature slowly. Stirring was continued for an additional 15 minutes. The reaction was neutralized by quenching with 10 mL of aqueous saturated sodium bicarbonate solution, most of the solvents were evaporated under reduced pressure and the organic residue was extracted into ethyl acetate, washed with water, dried over $MgSO_4$ (or $Na_2SO_4$) and concentrated under reduced pressure to give 13.8 g of a pale oily material contaminated with white solid. The oily fraction was dissolved into hexanes and the white solid was separated by filtration and identified to be one of the side products, 2,2-bis[(3,5-dimethyl-4-hydroxy)thio phenyl]-propane, 2.12 g. The oily fraction was reconcentrated and partitioned over a flash column packed with $SiO_2$—H (Merck), eluted with 2% tert-butyl alcohol in hexanes. Yield was 5.0 g of the desired product (12 mmoles, 41.1% based upon the thio phenol starting material used).

Examples 3–38 were prepared by a similar method to that described in the preparation of Examples I and II. Isolation yields are given.

EXAMPLE 3

2,6-Dimethyl-4-mercaptophenol m.p. = 82°–83° C.;
MS (CI): m/e = 155 for $(M+H)^+$;
IR (KBr) $\nu_{max}$: 3374 (br), 1476 (s), 1332 (s), 1191 (s), 852 (s), 464 (s) $cm^{-1}$;
$^1H$ NMR (CDCl$_3$) δ: 6.96 (2H, s), 4.67 (1H, s), 3.31 (1H, s), 2.18 (6H, s);
$^{13}C$ NMR (CDCl$_3$) δ: 151.0, 131.2, 124.1, 118.9, 15.7;
Anal. Calcd. for $C_8H_{10}OS$: C, 62.30; H, 6.54.
Found: C, 62.58; H, 6.57.

EXAMPLE 4

2,5-Dimethyl-4-mercaptophenol m.p. = 85°–86° C.;
MS (CI): m/e = 155 for $(M+H)^+$;
IR (KBr) $\nu_{max}$: 3370 (br)1, 1500 (s), 1454 (s), 1394 (s), 1374 (s), 1264 (s), 1160 (s), 1140 (s), 876 (s), 628 (s) $cm^{-1}$;
$^1H$ NMR (CDCl$_3$) δ: 7.08 (1H, s), 6.59 (1H, s), 4.90 (1H, br.s), 3.09 (1H, s), 2.26 (3H, s), 2.15 (3H, s);
$^{13}C$ NMR (CDCl$_3$) δ: 152.4, 136.4, 133.8, 122.2, 119.9, 117.0, 20.9, 15.1;
Anal. Calcd. for $C_8H_{10}OS$: C, 62.30; H, 6.54.
Found: C, 62.39; H, 6.44.

EXAMPLE 5

Bis(2,3-dimethyl-4-hydroxyphenyl) sulfide $^1H$ NMR (CDCl$_3$) δ: 6.78 (1H, d, J=8.3 Hz), 6.53 (1H, d, J=8.3 Hz), 4.6 (1H, s), 2.30 (3H, s), 2.18 (3H, s)

EXAMPLE 6

5,6,7,8-Tetrahydro-4-mercapto naphthalenol m.p. = 71.5°–72.1° C.;
MS (CI): m/e = 181 for $(M+H)^+$;
IR (KBr) $\nu_{max}$: 3320 (br), 2938 (m), 1446 (s), 1420 (s), 1322 (s), 1252 (s), 804 (s) $cm^{-1}$;
$^1H$ NMR (CDCl$_3$) δ: 7.04 (1H, d, J=8.3 Hz), 6.52 (1H, d, J=8.3 Hz), 5.07 (1H, s), 3.08 (1H, s), 2.81–2.59 (4H.m), 1.83–1.77 (4H, m);
$^{13}C$ NMR (CDCl$_3$) δ: 152.1, 137.6, 128.9, 124.9, 120.8, 112.5, 28.8, 23.3, 22.6, 22.0;
Anal Calcd. for $C_{10}H_{12}SO$: C, 66.63; H, 6.71.
Found: C, 66.38; H, 6.52.

EXAMPLE 7

2-Methyl-4-mercaptophenol m.p.=38°-39° C.;

MS (CI): m/e=141 for (M+H)+;

IR (KBr) $\nu_{max}$: 3200 (br), 1600 (m), 1500 (s), 1400 (s), 1235 (s), 1218 (s), 1102 (s), 805 (s) cm$^{-1}$;

$^1$H NMR (CDCl$_3$) δ: 7.10 (1H, d, J=1.5 Hz), 7.02 (1H, dd, J=2.8 Hz), 6.64 (1H, d, J=8 Hz), 5.30 (1H, br), 3.35 (1H, s), 2.18 (3H, s);

$^{13}$C NMR (CDCl$_3$) δ: 152.6, 133.8, 129.8, 125.1, 119.6, 115.7, 15.6;

Anal. Calcd. for C$_7$H$_8$SO: C, 59.97; H, 5.75.
Found: C, 60.15; H, 5.72.

EXAMPLE 8

3-Methyl-4-mercaptophenol m.p.=49°-50° C.;

MS (CI): m/e=141 for (M+H)+;

IR (KBr) $\nu_{max}$: 3214 (br), 2980 (br), 2936 (br), 1594 (s), 1482 (s), 1454 (s), 1292 (s), 1230 (s), 1170 (s), 634 (s), 572 (m) cm$^{-1}$;

$^1$H NMR (CDCl$_3$) δ: 7.16 (1H, d, J=8.3 Hz), 6.67 (1H, d, J=2.4 Hz), 6.56 (1H, dd, J=8.3, 2.6 Hz), 5.72 (1H, br.s), 3.13 (1H, s), 2.28 (3H, s);

$^{13}$C NMR (CDCl$_3$) δ: 153.9, 139.2, 135.8, 120.6, 117.4, 113.7, 21.3;

Anal Calcd. for C$_7$H$_8$SO: C, 59.97; H, 5.75
Found: C, 59.87; H, 5.72.

EXAMPLE 9

2,6-Bis(1,1-dimethylethyl)-4-[(1,1,4,8,12-pentamethyl-3,7,11-tridecatrienyl)thio]phenol MS (CI): m/e=279 for [(CH$_3$)$_2$CS+C$_{15}$H$_{25}$], and 238 for [HO(+Bu)$_2$C$_6$H$_3$S]+;

IR (KBr) $\nu_{max}$: 3639 (s), 2961 (br), 2920 (br), 1426 (s), 1237 (s), 654 (m) cm$^{-1}$;

$^1$H NMR (CDCl$_3$) δ: 7.35 (2H, s), 5.53 (1H, s), 5.38-5.09 (3H, m) 3.45 (2H, d, J=7.8 Hz), 2.13-1.95 (8H, m) 1.72 (3H, s) 1.68 (3H, s) 1.59 (6H s) 1.52 (6H, s), 1.43 (18H, s);

$^{13}$C NMR (CDCl$_3$) δ: 154.90, 139.17, 135.86, 135.20, 134.03, 131.22, 127.71, 124.35, 123.85, 122.13, 119.33, 84.21, 57.75, 39.60, 34.24, 39.67, 30.53, 30.25, 30.13, 28.30, 26.73, 26.36, 25.66, 17.67, 16.21, 15.99;

Anal. Calcd. for C$_{32}$H$_{52}$S$_2$O: C, 74.36; H, 10.14.
Found: C, 74.20; H, 10.33.

EXAMPLE 10

2,6-Dimethyl-4-[(1,1,4,8,12-pentamethyl-3,7-11-Tridecatrienyl)thio]phenol

MS (CI): m/e=205 for (C$_{15}$H$_{25}$)+, 195 for [HO(-Me)$_2$C$_6$H$_2$S(i Pr)]+, and 279 for [Me$_2$CS+C$_{15}$H$_{25}$];

IR (KBr) $\nu_{max}$: 3485 (br), 2922 (s), 1478 (s), 1195 (s), 1112 (s), 877 (m), 733 (m) cm$^{-1}$;

$^1$H NMR (CDCl$_3$) δ: 7.16 (1H, s), 5.28 (1H, dd, J=6.7, 7.8 Hz), 5.09-5.05 (2H, m), 4.71 (1H, s), 3.41 (2H, d, J=7.7 Hz), 2.21 (6H, s), 2.1-1.92 (8H, m), 1.71 (3H, s), 1.66 (3H, s), 1.57 (6H, s), 1.52 (6H, s);

$^{13}$C NMR (CDCl$_3$) δ: 153.3, 139.3, 137.5, 135.2, 131.2, 124.3, 123.8, 123.1, 123.0, 122.5, 119.2, 57.6, 39.6, 30.5, 28.3, 26.7, 26.3, 25.6, 17.6, 16.2, 15.9, 16.0, 15.7;

Anal. Calcd. for C$_{26}$H$_{40}$S$_2$O: C, 71.37; H, 9.58
Found: C, 71.24, H, 9.48

EXAMPLE 11

4-[[1-Methyl-1-[(3,7,11-trimethyl-2,6,10-dodecatrienyl)thio]ethyl]thio]phenol

MS (CI): m/e=205 for (C$_{15}$H$_{25}$)+, 167 for [HO(C$_6$H$_4$)S(i-pr)]+, and 279 for [(CH$_3$)$_2$CSC$_{15}$H$_{25}$]+;

IR (KBr) $\nu_{max}$: 3398 (br), 2923 (s), 1599 (s), 1494 (s), 1267 (s), 1110 (s), 1098 (s), 831 (s), 651 (s) cm$^{-1}$;

$^1$H NMR (CDCl$_3$) δ: 7.4 (2H, dd, J=9.5, 3.0 Hz), 6.77, (2H, dd, J=9.5, 3.0 Hz), 5.28 (1H, dd, J=6.7, 7.8 Hz), 5.1 (2H, br), 3.41 (2H, d, J=7.7 Hz), 2.11-1.93 (8H, m), 1.71 (3H, s), 1.66 (3H, s), 1.56 (6H, s), 1.52 (6H, s);

$^{13}$C NMR (CDCl$_3$) δ: 156.6, 139.5, 138.9, 135.3, 131.3, 124.4, 123.9, 123.5, 119.2, 115.5, 57.9, 39.7, 39.6, 30.5, 28.4, 26.7, 26.4, 25.7, 17.7, 16.2, 16.0;

Anal. Calcd. for C$_{24}$H$_{36}$S$_2$O: C, 71.23; H, 8.9
Found: C, 70.74, H, 8.98

EXAMPLE 12

2,5-Dimethyl-4-[[1-methyl-1-[(3,7,11-trimethyl-2,6,10-dodecatrienyl)thio]ethyl]thio]phenyl acetate MS (CI): m/e=237 for [AcOC$_6$H$_2$Me$_2$S(i-pr)]$^+$, 195 for [AcOC$_6$H$_2$Me$_2$S]$^+$, and 279 for [Me$_2$CSC$_{15}$H$_{25}$]$^+$;

IR (KBr) $\nu_{max}$: 2924 (s), 1764 (s), 1448 (s), 1364 (s), 1208 (s), 1186 (s), 1136 (s), 1106 (s), 1028 (s), 908 (m), 858 (m) cm$^{-1}$;

$^1$H NMR (CDCl$_3$) δ: 7.47 (1H, s), 6.91 (1H, s); 5.29 (1H, t, J=7.8 Hz), 5.09–5.05 (2H, m), 3.44 (2H, d, J=7.7Hz), 2.46 (3H, s), 2.29 (3H, s), 2.01 (3H, s), 2.0–1.95 (8H, m), 1.66 (3H, s), 1.60 (3H, s), 1.58 (6H, s), 1.55 (6H, s);

$^{13}$C NMR (CDCl$_3$) δ: 168.9, 149.9, 142.2, 140.7, 139.5, 135.2, 131.2, 129.3, 127.5, 124.3, 123.8, 123.4, 119.0, 58.9, 39.6, 39.5, 30.7, 28.4, 26.7, 36.3, 25.6, 21.3, 20.7, 17.6, 16.2, 15.9, 15.6;

Anal Calcd. for C$_{28}$H$_{42}$O$_2$S$_2$: C, 70.84; H, 8.92
Found: C, 70.92, H, 8.83

EXAMPLE 13

2,3-Dimethyl-4-[[1-methyl-1-[(3,7,11-trimethyl-2,6,10-dodecatrienyl)thio]ethyl]thio]phenyl acetate MS (CI): m/e=237 for [AcOC$_6$H$_2$Me$_2$S(i-Pr)]$^+$, and 279 for [Me$_2$CS(C$_{15}$H$_{25}$)]$^+$;

IR (KBr) $\nu_{max}$: 2922 (s), 1768 (s), 1462 (s), 1368 (s), 1210 (s), 1200 (s), 1178 (s), 1106 (s), 1066 (s), 884 (s), 758 (s) cm$^{-1}$;

$^1$H NMR (CDCl$_3$) δ: 7.50 (1H, d, J=8.4 Hz), 6.84 (1H, d, J=8.4 Hz), 5.28 (1H, t, J=7.7 Hz), 5.08 (2H, br), 3.44 (2H, d, J=7.7 Hz), 2.51 (3H, s), 2.31 (3H, s), 2.09 (3H, s), 1.95–2.05 (8H, m), 1.66 (3H, s), 1.60 (3H, s), 1.58 (6H, s), 1.52 (6H, s);

$^{13}$C NMR (CDCl$_3$) δ: 169.1, 149.9, 144.1, 139.5, 136.6, 135.3, 131.2, 129.7, 129.6, 124.4, 123.8, 119.2, 119.1, 58.9, 39.7, 39.6, 30.7, 28.4, 26.7, 26.4, 25.7, 20.8, 19.1, 17.7, 16.2, 16.0, 13.6;

Anal. Calcd. for C$_{28}$H$_{42}$O$_2$S$_2$: C, 70.84; H, 8.92
Found: C, 70.83, H, 8.73

EXAMPLE 14

2-Methyl-4-[1-methyl-1-[(3,7,11-trimethyl-2,6,10-dodecatrienyl)thio]ethyl]thio phenol MS (FAB): m/e=181 for [Me(HO)C$_6$H$_3$S(i-Pr)]$^+$, 205 for (C$_{15}$H$_{25}$)$^+$, and 279 for [Me$_2$CS(C$_{15}$H$_{25}$)]$^+$;

IR (KBr) $\nu_{max}$: 3422 (br), 2922 (s), 1492 (s), 1268 (s), 1106 (s), 816 (s), 656 (s) cm$^{-1}$;

$^1$H NMR (CDCl$_3$) δ: 7.29 (1H, s), 7.25 (1H, dd, J=2.1, 7.9 Hz), 6.71 (1H, d, J=8.2 Hz), 5.28 (1H, dd, J=6.9, 7.9 Hz), 5.09–5.05 (2H, br), 5.03 (1H, s), 3.42 (2H, d, J=7.8 Hz), 2.22 (3H, s), 2.1–1.9 (8H, m), 1.71 (3H, s), 1.66 (3H, s), 1.58 (6H, s), 1.52 (6H, s);

$^{13}$C NMR (CDCl$_3$) δ: 154.9, 140.0, 139.4, 136.2, 135.2, 131.3, 124.4, 124.0, 123.8, 123.2, 119.2, 115.0, 57.8, 39.7, 30.5, 28.3, 26.7, 26.3, 25.7, 17.7, 16.2, 16.0, 15.7;

Anal. Calcd. for C$_{25}$H$_{38}$S$_2$O: C, 71.72; H, 9.15.
Found: C, 71.66; H, 9.31.

EXAMPLE 15

3-Methyl-4-[[1-methyl-1-[(3,7,11-trimethyl-2,6,10-dodecatrienyl)thio]ethyl]thio]phenol acetate MS (FAB): m/e=223 for [AcO(Me)C$_6$H$_3$S(i-Pr)]$^+$, 205 for (C$_{15}$H$_{25}$)$^+$, and 279 for [Me$_2$CS(C$_{15}$H$_{25}$)]$^+$;

IR (KBr $\nu_{max}$: 2922 (s), 1768 (s), 1370 (s), 1202 (s), 1156 (s), 1106 (s), 1016 (s), 652 (s), 596 (s) cm$^{-1}$;

$^1$H NMR (CDCl$_3$) δ: 7.61 (1H, d, J=8.4 Hz), 6.99 (1H, d, J=2.6 Hz), 6.89 (1H, dd, J=2.5, 8.4 Hz), 5.28 (1H, t, J=7.8 Hz), 5.1 (2H, m), 3.44 (2H, d, J=7.7 Hz), (2.5 (3H, s), 2.27 (3H, s), 2.1–1.9 (8H, m), 1.70 (3H, s), 1.66 (3H, s), 1.60 (3H, s), 1.58 (6H, s);

$^{13}$C NMR (CDCl$_3$) δ: 151.2, 145.0, 139.6, 139.1, 135.2, 129.1, 124.4, 123.8, 123.2, 119.0, 59.1, 39.7, 39.6, 30.7, 28.4, 26.7, 26.3, 25.7, 21.8, 21.1, 17.7, 16.2, 16.1;

Anal. Calcd. for C$_{27}$H$_{40}$S$_2$O$_2$: C, 70.39; H, 8.75
Found: C, 70.69; H, 8.69

EXAMPLE 16

5,6,7,8-Tetrahydro-4-[[1-methyl-1-[(3,7,11-trimethyl-2,6,-10-dodecatrienyl) thio]ethyl]thio]-1-naphthalenol MS (FAB): m/e=221 for [(HO)C$_{10}$H$_{10}$S(Me)$_2$C]$^+$, 205 for (C$_{15}$H$_{25}$)$^+$, and 279 for [(Me)$_2$CS(C$_{15}$H$_{25}$)]$^+$;

IR (KBr $\nu_{max}$: 3416 (br), 2926 (s), 1576 (s), 1450 (s), 1440 (s), 1306 (s), 1276 (s), 1106 (s), 810 (s) cm$^{-1}$;

$^1$H NMR (CDCl$_3$) δ: 7.33 (1H, d, J=8.2 Hz), 6.60 (1H, d, J=8.2 Hz), 5.28 (1H, t, J=6.7 Hz), 5.09–5.05 (2H, m), 4.94 (1H, s), 3.44 (2H, d, J=7.7 Hz), 2.97 (2H, t, J=5.8 Hz), 2.62 (2H, t, J=6.0 Hz), 2.1–1.9 (8H, m), 1.8–1.7 (4H, m), 1.71 (3H, s), 1.67 (3H, s), 1.58 (6H, s), 1.52 (6H, s);

$^{13}$C NMR (CDCl$_3$) δ: 154.5, 144.2, 139.4, 136.8, 135.3, 131.3, 124.4, 124.2, 123.9, 123.2, 119.2, 111.9, 58.8, 39.7, 39.6, 30.6, 29.5, 29.4, 28.4, 28.0, 26.7, 26.4, 25.7, 23.3, 22.3, 21.2, 17.7, 16.2, 16.0;

Anal. Calcd. for C$_{28}$H$_{42}$S$_2$O: C, 73.31; H, 9.23.

Found: C, 73.23; H, 9.16.

EXAMPLE 17

2-(1,1-dimethylethyl)-4-mercaptophenol

MS (CI): m/e=182 for $[C_{10}H_{14}OS]^+$;

IR (KBr) $\nu_{max}$: 3536 (m), 2958 (s), 1590 (m), 1494 (s), 1484 (s), 1398 (s), 1256 (s), 1184 (s), 1084 (s), 812 (s), 654 (m) cm$^{-1}$;

$^1$H NMR (CDCl$_3$) δ: 7.45–6.02 (2H, m), 6.56 (1H, dd, J=8.3, 10.6 Hz), 4.84 (1H, s), 3.34 (1H, s), 1.36 (9H, s);

$^{13}$C NMR (CDCl$_3$) δ: 153.2, 137.2, 130.6, 129.9, 119.4, 117.3;

Anal. Calcd. for $C_{10}H_{14}OS$: C, 65.89; H, 7.74.
Found: C, 64.96; H, 7.41.

EXAMPLE 18

2-(1-methylpropyl)-4-mercaptophenol

MS (CI): m/e=182 for $[C_{10}H_{14}OS]^+$;

IR (KBr) $\nu_{max}$: 3436 (s), 2980 (s), 1600 (m), 1500 (s), 1465 (s), 1417 (s), 1255 (s), 1180 (s), 1115 (s), 813 (s), cm$^{-1}$;

$^1$H NMR (CDCl$_3$) δ: 7.13 (1H, d, J=2.3 Hz), 7.02 (1H, dd, J=2.4 8.3 Hz), 6.63 (1H, d, J=8.3 Hz), 5.06 (1H, s), 3.38 (1H, s), 2.91 (1H, sextet, J=7.0 Hz), 1.6 (2H, m), 1.19 (3H, d, J=6.8 Hz), 0.86 (3H, t, J=7.2 Hz);

$^{13}$C NMR (CDCl$_3$) δ: 151.96, 134.61, 130.34, 129.60, 119.85, 116.24, 33.93, 29.76, 20.38, 12.16;

Anal. Calcd. for $C_{10}H_{14}OS$: C, 65.89; H, 7.74
Found: C, 66.11; H. 7.70.

EXAMPLE 19

2-(1,1-Dimethylethyl)-4-[[1-methyl-1-[(3,7,11-trimethyl-2,6,10-dodecatrienyl)thio]ethyl]thio]phenol MS (FAB): m/e=223 for $[t\text{-}Bu(HO)C_6H_3SCMe_2]^+$, 181 for $[t\text{-}Bu(HO)C_6H_3S]^+$, and 279 for $[Me_2CS(C_{15}H_{25})]^+$;

IR (KBr) $\nu_{max}$: 3380 (br), 2962 (s), 2922 (s), 1590 cm$^{-1}$;

$^1$H NMR (CDCl$_3$) δ: 7.43 (1H, d, J=2.1 Hz), 7.24 (1H, m), 6.61 (1H, d, J=8.1 Hz), 5.28 (1H, t, J=6.7 Hz), 5.08 (2H, m), 5.04 (1H, s), 3.42 (2H, , J=7.7 Hz), 2.19–1.93 (8H, m), 1.71 (3H, s) 1.66 (3H d J=0.6 Hz) 1.52 (6H, s), 1.58 (6H, s), 1.38 (9H, s);

$^{13}$C NMR (CDCl$_3$) δ: 155.34, 139.36, 136.52, 136.23, 135.90, 135.26, 131.32, 124.38, 123.09, 119.22, 116.63, 57.89, 39.70, 39.60, 34.52, 30.51, 29.49, 28.24, 26.73, 25.71, 17.71, 16.23, 16.03;

Anal. Calcd. for $C_{28}H_{41}OS_2$: C, 72.99; H, 9.62.
Found: C, 72.97; H, 9.56.

EXAMPLE 20

2-(1-Methylpropyl)-4-[[1-methyl-1-[3,7,11-trimethyl-2,6,10-dodecatrienyl)thio]ethyl]thio]phenol MS (FAB): m/e=223 for $[(EtMeCH)(HO)C_6H_3SCMe_2]^+$, 181 for $[(EtMeCH)(HO)C_6H_3S]^+$, and 279 for $[Me_2CS(C_{15}H_{25})]^+$;

IR (KBr) $\nu_{max}$: 3406 (br), 2962 (s), 2924 (s), 2874 (s), (s), 1452 (m), 1104 (s), 816 (m), 654 (m) cm$^{-1}$;

$^1$H NMR (CDCl$_3$) δ: 7.38 (1H, d, J=2.2 Hz), 7.21 (1H, dd, J=B.1, 2.2 Hz), 6.69 (1H, d, J=8.2 Hz), 5.28 (1H, t, J=7.9 Hz), 5.08–5.05 (2H, m), 4.97 (1H, s), 3.42 (2H, d, J=1.66 Hz), (3H, s), 1.59 (6H, s), 1.50 (6H, s), 1.20 (3H, d, J=6.9 Hz), 0.83 (3H, t, J=7.4 Hz);

$^{13}$C NMR (CDCl$_3$) δ: 154.2, 139.4, 136.6, 135.6, 135.3, 133.4, 131.3, 124.4, 123.9, 123.4, 119.2, 115.4, 57.9, 39.7, 17.7, 16.2, 16.0, 12.1;

Anal Calcd. for $C_{28}H_{41}OS$: C, 72.99; H, 9.62.
Found: C, 72.80; H, 9.28.

EXAMPLE 21

2-Phenyl-4-[[1-methyl-1-[(3,7,11-trimethyl-2,6,10-dodecatrienyl)thio]phenol

MS (FAB): m/e=243 for $[Ph(HO)C_6H_3SCMe_2]^+$, 201 for $[Ph(HO)C_6H_3S]^+$, 201 for $[Ph(HO)(C_6H_3S]^+$, and 279 for $[Me_2CS(C_{15}H_{25})]^+$;

IR (KBr) $\nu_{max}$: 3548 (br), 2964 (s), 2922 (s), 1662 (m), 1604 (m), 1474 (s), 1446 (s), 1226 (m), 1172 (s), 1108 (s), 758 (s), 700 (s), 620 (m), 596 (m) cm$^{-1}$;

$^1$H NMR (CDCl$_3$) δ: 7.51–7.36 (7H, m), 6.93 (1H, dd, J=0.6, 8.5 Hz), 5.42 (1H, s), 5.28 (1H, t, J=8.0 Hz), 5.07 (2H, t, J=6.9 Hz), 3.43 (2H, d, J=7.8 Hz), 2.11–1.94 (8H, m), 1.69 (3H, s), 1.66 (3H, s), 1.61 (6H, s), 1.58 (6H, s);

$^{13}$C NMR (CDCl$_3$) δ: 153.6, 139.5, 139.3, 138.2, 136.3, 135.3, 131.3, 129 4, 129.4, 129.0, 128.3, 128.1, 124.4, 123.8, 123.6, 119.1, 116.1, 58.1, 39.7, 39.6, 30.6, 28.4, 26.7, 26.4, 25.7, 17.7, 16.2, 16.0;

Anal. Calcd. for C$_{30}$H$_{40}$OS$_2$: C, 74.95; H, 8.39.
Found: C, 74.75; H, 8.34.

EXAMPLE 22

3,5-Dimethyl-4-mercaptophenol m.p. = 100°–102° C.;
MS (CI): m/e = 155 for (M+H)$^+$;
IR (KBr) $\nu_{max}$: 3264 (br), 1586 (s), 1466 (s), 1438 (s), 1376 (m), 1348 (m), 1308 (s), 1164 (s), 1024 (s), 850 (s);
$^1$H NMR (CDCl$_3$) δ: 6.57 (2H, s), 5.52 (1H, br) 2.95 (1H, s), 2.31 (6H, s);
$^{13}$C NMR (CDCl$_3$) δ: 153.8, 139.8, 121.6, 115.9, 23.0;
Anal. Calcd. for C$_8$H$_{10}$OS: C, 62.30; H, 6.54.
Found: C, 62.51; H, 6.43.

EXAMPLE 23

1-[(3,5-Dimethyl-4-hydroxy)thiophenyl]-1-[thio(3,7-11-trimethyl-2,6,10-dodecatrienyl]cyclohexane MS (FAB): m/e = 153 for [Me$_2$(OH)C$_6$H$_2$S$^+$], 235 for [Me$_2$(OH)C$_6$H$_2$S C$_6$H$_{10}$], and 319 for [C$_6$H$_{10}$S+C$_{15}$H$_{25}$];
IR (KBr) $\nu_{max}$: 3792 (br), 2930 (s), 2854 (s), 1478 (s), 1446 (s), 1192 (s), 1112 (s), 1008 (m), 872 (m), 732 (m);
$^1$H NMR (CDCl$_3$) δ: 7.15 (2H, s), 5.27 (1H, dd, J = 8.8, 7.7 Hz), 5.07 (2H, m), 4.7 (1H, br), 3.34 (2H, d, J = 7.83 Hz), 2.20 (6H, s), 2.1–1.9 (8H, m), 1.70 (3H, s), 1.65 (3H, s), 1.56 (3H, s), 1.8–1.4 (10H, m);
$^{13}$C NMR (CDCl$_3$) δ: 153.3, 139.3, 137.8, 135.3, 131.3, 124.4, 123.9, 122.9, 121.4, 119.1, 63.8, 39.7, 39.6, 37.3, 26.7, 26.4, 25.7, 25.4, 22.6, 17.7, 16.3, 16.0, 15.8;
Anal. Calcd. for C$_{29}$H$_{44}$OS$_2$: C, 73.67; H, 9.38.
Found: C, 73.65; H, 8.86.

EXAMPLE 24

2,6-Dimethyl-4-[[1-methyl-1-[(5,9,13-trimethyl-4,8,12-tetradodecatrienyl)thio]ethyl]thio]phenol MS (CI): m/e = 460 for M+;
IR (KBr) $\nu_{max}$: 2964 (s), 2922 (s), 2856 (m), 1478 (s), 1448 (m), 1194 (s), 1110 (s);
$^1$H NMR (CDCl$_3$) δ: 7.14 (2H, s), 5.16–5.05 (3H, m), 4.74 (1H, s, D$_2$O exchangeable), 2.75 (2H, t, J = 7.4 Hz), 2.21 (6H, s), 2.2–1.97 (8H, m), 1.69 (3H, s), 1.66 (3H, s), 1.58 (6H, s), 1.51 (6H, s);

$^{13}$C NMR (CDCl$_3$) δ: 153.38 137.62 136.02 135.02, 31.29, 124.40, 124.18, 123.49, 123.11, 122.56, 57.44, 39.74, 30.66, 29.72, 29.56, 27.59, 26.77, 26.67, 26.52, 25.72, 17.72, 16.14, 16.02, 15.81;
Anal. Calcd. for C$_{25}$H$_{44}$S$_2$O: C, 72.99; H, 9.62.
Found: C, 72.90; H, 9.61.

EXAMPLE 25

[[1-Methyl-1-[(3,7,11-trimethyl-2,6,10-dodecatrienyl)thio]ethyl]thio]benzene MS (CI): m/e = 205 for [C$_{15}$H$_{25}$]$^+$, and 151 for [C$_6$H$_5$SCMe$_2$]$^+$;
IR (KBr) $\nu_{max}$: 2964 (s), 2922 (s), 2854 (m), 1438 (m), 1108 (m), 750 (s), 692 (m);
$^1$H NMR (CDCl$_3$) δ: 7.65–7.55 (2H, m), 7.39–7.30 (3H, m), 5.32–5.27 (1H, m), 5.09–5.05 (2H, m), 3.44 (2H, d, J = 7.8 Hz), 2.12–1.93 (8H, m), 1.71 (3H, s), 1.67 (3H, s), 1.58 (6H, s), 1.55 (6H, s);
$^{13}$C NMR (CDCl$_3$) δ: 139.50, 136.95, 135.26, 132.46, 131.29, 129.08, 129.00, 128.55, 128.47, 124.38, 123.85, 119.12, 58.05, 39.71, 39.61, 30.77, 28.43, 26.74, 26.60, 26.36, 25.72, 17.72, 16.22, 16.04;
Anal Calcd. for C$_{24}$H$_{36}$S$_2$: C, 74.16; H, 9.34.
Found: C, 74.42; H, 9.44.

EXAMPLE 26

Propanoic Acid, 2-[(4-hydroxy-3,5-dimethylphenyl)thio]-2-[(3,7,11-trimethyl-2,6,10-dodecatrienyl)thio]methyl ester MS (CI): m/e = 476 for M+, and 323 for [C$_{15}$H$_{25}$SCH$_3$CCOOMe]$^+$;
IR (KBr) $\nu_{max}$: 3494 (m), 2928 (s), 2864 (s), 1726 (s), 1478 (s), 1446 (m), 1374 (m), 1248 (s), 1196 (s], 1112 (s), 596 (m);
$^1$H NMR (CDCl$_3$) δ: 7.08 (2H, s), 5.2 (1H, m), 5.0 (1H, m), 4.8 (1H, m), 3.67 (3H, s), 3.44 (2H, dq, J = 5.7, 13.5Hz), 2.15 (6H, s), 2.03–1.83 (8H, m), 1.68 (3H, s), 1.59 (3H, s), 1.54 (6H, m), 1.56 (3H, s);
$^{13}$C NMR (CDCl$_3$) δ: 171.3, 153.9, 140.8, 137.5, 131.3, 124.3, 123.7, 123.4, 120.6, 117.8, 60.9, 52.8, 39.7, 39.6, 29.4, 27.5, 26.7, 26.3, 25.7, 25.2, 16.2, 16.0, 15.8.
Anal. Calcd. for C$_{27}$H$_{40}$O$_3$S$_2$ C, 68.02; H, 8.46.
Found: C, 66.70; H, 8.35 (H$_2$O = 0.3%)

EXAMPLE 27

Propanoic Acid, 2-[(4-hydroxy-3,5-dimethylphenyl)thio]-2-[(3,7,11-trimethyl-2,6,10-dodecatrienyl)thio]ethyl ester MS (CI): m/e=490 for M$^+$;
IR (KBr) $\nu_{max}$: 3492 (m), 2978 (s), 2926 (s), 2856 (m), 1712 (s), 1478 (s), 1446 (s), 1374 (m), 1282 (m), 1246 (s), 1196 (s), 1110 (s);
$^1$H NMR (CDCl$_3$) δ: 7.12 (2H, m), 5.24 (1H, m), 5.05 (2H, m), 4.98 (1H, s, D$_2$O exchangeable), 4.14 (2H, dq, J=7.2, 10.8 Hz), 3.48 (2H, dq, J=7.9, 11.9 Hz), 2.17 (6H, s), 2.1–1.9 (8H, m), 1.68 (3H, d, J=0.9 Hz), 1.63 (3H, d, J=0.9 Hz), 1.58 (3H, s), 1.56 (6H, s), 1.24 (3H, d, J=5.3 Hz);
$^{13}$C NMR (CDCl$_3$) δ: 170.9, 153.9, 140.8, 137.5, 135.3, 131.3, 124.4, 123.8, 123.4, 120.6, 117.9, 61.9, 60.9, 39.9, 39.7, 39.6, 31.9, 29.4, 26.7, 26.3, 25.7, 25.2, 17.7, 16.2, 16.0, 15.8, 14.1;
39.9, 39.6, 32.1, 31.8, 30.6, 28.5, 28.0, 26.6, 25.6, 17.6, 17.5, 16.1, 15.9, 15.7, 14.3;
Anal. Calcd. for C$_{30}$H$_{46}$OS$_2$: C, 74.01; H, 9.52.
Found: C, 74.54; H, 9.97.

EXAMPLE 29

2,6-Dimethyl-4-[[1-methyl-1-[(3,7,11,15-tetramethyl-2,6,10,14-hexadecatetraenyl)thio]ethyl]thio]phenyl MS (CI)=m/e=500 for M$^+$;
IR (KBr) $\nu_{max}$: 2964 (s), 2924 (s), 2856 (s), 1478 (s), 1448 (s), 1378 (m), 1228 (m), 1194 (s), 1110 (s);
$^1$H NMR (CDCl$_3$) δ: 7.12 (2H, s), 5.25 (1H, br. t, J=7.84 Hz), 5.05 (3H, m), 4.81 (1H, br.s, D$_2$O exchangeable), 3.38 (2H, d, J=7.7 Hz), 2.17 (6H, s), 2.08–1.72 (12H, m), 1.68 (3H, s), 1.63 (6H, s), 1.54 (6H, s), 1.49 (6H, s);
$^{13}$C NMR (CDCl$_3$) δ: 153.5, 139.5, 137.6, 135.6, 125.1, 124.4, 124.3, 123.2, 122.5, 120.0, 119.9, 119.3, 119.2, 57.7, 39.8, 39.7, 32.0, 30.6, 28.3, 26.7, 26.5, 26.4, 25.7, 23.4, 17.7, 16.3, 16.1, 15.9.
Anal. Calcd. for C$_{31}$H$_{48}$OS$_2$: C, 74.34; H, 9.66.
Found: C, 74.55; H, 9.69.

EXAMPLE 30

2-Methyl-4-[[1-methyl-1-[(3,7,11-trimethyl-2,6,10-dodecatrienyl)thio]ethyl]thio]phenyl,3-pyridine carboxylate Anal. Calcd. for C$_{28}$H$_{42}$O$_3$S$_2$: C, 68.53; H, 8.63.
Found: C, 68.45; H, 8.61.

EXAMPLE 28

2-Methyl-4-[[1-methyl-1-[(3,7,11,15-tetramethyl-2,6,10,14-hexadecatetraenyl)thio]ethyl]thiophenol MS (CI): m/e=486 for M$^+$;
IR (KBr) $\nu_{max}$: 3416 (m), 2964 (s), 2924 (s), 2856 (s), 1492 (s), 1450 (s), 1396 (m), 1378 (m), 1266 (m), 1216 (m), 1106 (s), 816 (m), 760 (s);
$^1$H NMR (CDCl$_3$) δ: 7.25 (1H, s), 7.19 (1H, dd, J=1.9, 8.1 Hz), 6.66 (1H, d, J=8.2 Hz), 5.46 (1H, br. s, D$_2$O exchangeable), 5.25 (1H, br. t, J=7.8 Hz), 5.05 (3H, m), 3.40 (2H, d, J=7.7 Hz), 2.17 (3H, s), 2.1–1.9 (12H, m), 1.67 (3H, s), 1.57 (6H, s), 1 55 (6H, s), 1.49 (6H, s);
$^{13}$C NMR (CDCl$_3$) δ: 155.0, 139.9, 139.4, 136.1, 135.3, 124.9, 124.6, 124.3, 124.1, 123.8, 119.7, 119.0, 114.9, 57.7, MS (CI)=m/e=523 for M$^+$;
IR (KBr) $\nu_{max}$: 2964 (s), 2922 (s), 2856 (m), 1746 (s), 1590 (m), 1484 (s), 1448 (m), 1420 (m), 1274 (s), 1224 (s), 1174 (s), 1118 (s), 1108 (s), 1080 (s), 1020 (s);
$^1$H NMR (CDCl$_3$) δ: 9.34 (1H, d, J=2.1 Hz), 8.80 (1H, dd, J=1.7, 4.8 Hz), 8.39 (1H, dd, J=1.8, 3.9 Hz), 7.41 (2H, m), 7.08 (1H, d, J=8.1 Hz), 5.23 (1H, m), 5.02 (2H, m), 3.39 (2H, d, J=7.6 Hz), 2.18 (3H, s), 2.02–1.82 (8H, m), 1.67 (3H, s), 1.60 (3H, s), 1.52 (12H, s);
$^{13}$C NMR (CDCl$_3$) δ: 163.3, 154.2, 151.4, 150.0, 139.7, 139.6, 137.6, 135.6, 135.3, 131.2, 130.4, 130.3, 125.3, 124.4, 123.8, 123.5, 121.9, 119.0, 58.1, 39.7, 39.6, 30.8, 28.4, 26.7, 26.6, 26.4, 25.7, 17.7, 16.3, 16.0.
Anal. Calcd. for C$_{31}$H$_{41}$NO$_2$S: C, 71.08; H, 7.89; N, 2.67.
Found: C, 71.40; H, 7.94; N, 2.50.

EXAMPLE 31

2,6-Dimethyl-4-[[[1-(3,7,11-trimethyl-2,6,10-dodeca-trienyl)thio]cyclopentyl]thio]phenol MS (CI)=m/e=458 for M+;
IR (KBr) $\nu_{max}$: 2964 (s), 2924 (s), 2856 (s), 1478 (s), 1446 (S), 1380 (m), 1226 (m), 1194 (s), 1112 (s);
$^1$H NMR (CDCl$_3$) δ: 7.18 (2H, s), 5.29 (1H, dd, J=6.9, 7.9 Hz), 5.07 (2H, m), 4.73 (1H, s), 3.43 (2H, d, J=7.8 Hz), 2.213 (6H, s), 2.12–1.84 (16H, m), 1.72 (3H, s), 1.66 (3H, s), 1.57 (6H, s);
$^{13}$C NMR (CDCl$_3$) δ: 153.3, 139.1, 137.1, 135.2, 131.3, 124.4, 123.9, 123 1, 123.1, 119.4, 68.4, 40.4, 39.7, 39.6, 28.9, 26.7, 26.4, 25.7, 24.0, 17.7, 16.3, 16.0, 15.8;
Anal. Calcd. for C$_{28}$H$_{42}$OS$_2$: C, 73.31; H, 9.23
Found: C, 73.47; H, 9.39.

EXAMPLE 32

2,6-Dimethyl-4-[[[1-(3,7,11-trimethyl-2,6,10-dodeca-trienyl)thio]cycloheptyl]thio]phenol MS (CI)=m/e=486 for M+;
IR (KBr) $\nu_{max}$: 2966 (m), 2924 (s), 2854 (s), 1478 (s), 458 (s), 1444 (s), 1380 (m), 1226 (m), 1194 (s), 1112 (m);
$^1$H NMR (CDCl$_3$) δ: 7.12 (2H, s), 5.25 (1H, dd, J=6.9, 7.9 Hz), 5.04 (2H, m), 4.70 (1H, s, D$_2$O exchangeable), 3.36 (2H, d, J=7.8 Hz), 2.18 (6H, s), 2.17–1.76 (8H, m), 1.67 (3H, s), 1.63 (3H, s), 1.58–1.39 (12H, m), 1.55 (6H, s).
$^{13}$C NMR (CDCl$_3$) δ: 153.3, 139.2, 137.7, 135 2, 131.2 133.1, 124.3, 123.8, 122.9, 122.1, 119.0, 67.9, 40.1, 39.7, 39.6, 29.7, 27.7, 26.9, 26.7, 26.4, 25.7, 22.9, 17.6, 16.3, 15.9, 15.8;
Anal. Calcd. for C$_{30}$H$_{46}$OS$_2$ C, 74.02; H, 9.52.
Found: C, 73.75; H, 9.54.

EXAMPLE 33

Propanoic Acid, 2-[(4-hydroxy-3,5-dimethylphenyl)thio]-2-[(3,7,11,15-tetramethyl-2,6,10,14-hexadecatetraenyl)thio]ethyl ester MS (CI)=m/e=558 for M+;
$^1$H NMR (CDCl$_3$) δ: 7.16 (2H, s), 5.26 (1H, t, J=7.9, Hz), 5.09 (3H, m), 4.80 (1H, s), 4.19 (2H, dq, J=3.0, 7.2 Hz), 3.52 (2H, dq, J=7.9, 12.0 Hz), 2.21 (6H, s), 2.11–1.98 (12H, m), 1.66 (3H, s), 1.70 (3H, s), 1.60 (6H, s), 1.59 (3H, s), 1.58 (3H, s);
Anal. Calcd. for C$_{33}$H$_{50}$O$_3$S$_2$: C, 70.92; H, 9.02.
Found: C, 69.19; H, 8.72.

EXAMPLE 34

Propanoic Acid, 2-[(4-hydroxy-3,5-dimethylphenyl)thio]-2-(3,7,11,15-tetramethyl-2,6,10,14-hexadecatetraenyl)thio]methyl ester MS (CI)=m/e=544 for M+;
$^1$H NMR (CDCl$_3$) δ: 7.12 (2H, s), 5.23 (1H, t, J=7.2, Hz), 5.07 (3H, m), 4.75 (1H, s, D$_2$O exchangeable), 3.71 (3H, s), 3.46 (2H, dq, J=12.1, 4.7 Hz), 2.19 (6H, s), 2.07–1.90 (12H, m), 1.68 (3H, s), 1.65 (3H, s), 1.59 (3H, s), 1.58 (3H, s), 1.56 (3H, s), 1.53 (3H, s);
Anal Calcd. for C$_{32}$H$_{48}$O$_3$S$_2$: C, 70.54; H, 8.88.
Found: C, 69.72; H, 8.68.

EXAMPLE 35

3,4-Dimethyl-1-[[1-methyl-1-[3,7,11-trimethyl-2,6,10-dodecatrienyl)thio]ethyl]thio]benzene MS (FAB): m/e=179 for [Me$_2$C$_6$H$_3$SCMe$_2$]+;
IR (KBr) $\nu_{max}$: 2966 (s), 2920 (s), 2856 (s), 1450 (m), 1378 (m), 1108 (m), 816 (m);
$^1$H NMR (CDCl$_3$) δ: 7.34–7.24 (2H, m), 7.08 (1H, d, J=7.7 Hz), 5.29 (1H, dd, J=6.8–7.8 Hz), 5.09–5.05 (2H, m), 3.43 (2H, d, J=7.8 Hz), 2.24 (6H, s), 2.12–1.93 (8H, m), 1.72 (3H, s), 1.68 (3H, s), 1.58 (6H, s), 1.53 (6H, s);
$^{13}$C NMR (CDCl$_3$) δ: 139.40, 139.30, 138.14, 137.86, 136.77, 135.24, 134.49, 131.27, 129.77, 129.10, 124.37, 123.87, 119.26, 119.18, 57.79, 39.70, 39.61, 30.71, 28.38, 28.31, 26.74, 26.36, 25.70, 19.68, 19.58, 17.70, 16.22, 16.12, 16.03;

Anal. Calcd. for $C_{26}H_{40}S_2$: C, 74.94; H, 9.67.
Found: C, 75.11; H, 9.84.

EXAMPLE 36

4-Fluoro-1-[[1-methyl-1-[(3,7,11-trimethyl-2,6,10-dodecatrienyl)thio]ethyl]thio]benzene MS (CI): m/e=279 for $[Me_2CS(C_{15}H_{25})]^+$, 205 for $(C_{15}H_{25})^+$, 169 for $(FC_6H_4SCMe_2)^+$;

IR (KBr) $\nu_{max}$: 2966 (s), 2922 (s), 2854 (m), 1588 (m), 1488 (s), 1224 (s), 1110 (m), 832 (m);

$^1$H NMR (CDCl$_3$) δ: 7.61–7.48 (2H, m), 7.06–6.97 (2H, m), 5.31–5.25 (1H, m), 5.10–5.05 (2H, m), 3.41 (2H, d, J=7.7 Hz), 2.12–1.93 (8H, m), 1.74 (3H, s), 1.70 (3H, s), 1.58 (6H, s), 1.52 (6H, s);

$^{13}$C NMR (CDCl$_3$) δ: 165.19, 161.89, 139.60, 139.00, 138.89, 135.30, 131.30, 127.78, 127.72, 124.35, 123.80, 118.99, 115.74, 115.44, 58.15, 39.70, 39.59, 30.57, 28.38, 26.73, 26.33, 25.70, 17.70, 16.21, 16.03;

Anal. Calcd. for $C_{24}H_{35}SF$: C, 70.88; H, 8.67.
Found: C, 71.14; H, 8.81.

EXAMPLE 37

5-[[1-Methyl-1-[(3,7,11-trimethyl-2,6,10-dodecatrienyl)thio]ethyl]mercapto-2-hydroxybenzoic acid, methyl ester MS (DCI): m/e=225 for $[(HOC_6H_3COOCH_3)S(i-Pr)]^+$;

IR (KBr) $\nu_{max}$: 2962 (s), 2922 (s), 2854 (m), 1680 (s), 1476 (m), 1440 (s), 1326 (s), 1288 (s), 1244 (m), 1210 (s), 1104 (m), 560 (s);

$^1$H NMR (CDCl$_3$) δ: 10.87 (1H, s), 7.97 (1H, t, J=2.5 Hz), 7.57 (1H, dd, J=2.2, 8.6 Hz), 6.90 (1H, d, J=8.6 Hz), 5.26 (1H, t, J=7.7 Hz), 5.03 (2H, m), 3.91 (3H, s), 3.38 (2H, d, J=7.8 Hz), 2.09–1.90 (8H, m), 1.68 (3H, d, J=0.6 Hz), 1.62 (3H, d, J=0.6 Hz), 1.54 (6H, s), 1.49 (6H, s).

$^{13}$C NMR (CDCl$_3$) δ: 170.1, 162.4, 144.4, 139.6, 139.0, 135.3, 131.3, 124.3, 123.8, 122.1, 118.9, 117.9, 112.5, 58.3, 52.4, 39.672, 39.63, 30.4, 28.4, 26.7, 26.3, 25.7, 17.7, 16.1, 16.0;

Anal. Calcd. for $C_{26}H_{38}O_3S_2$: C, 67.49; H, 8.28.
Found: C, 67.99; H, 8.19.

EXAMPLE 38

Figure 4:
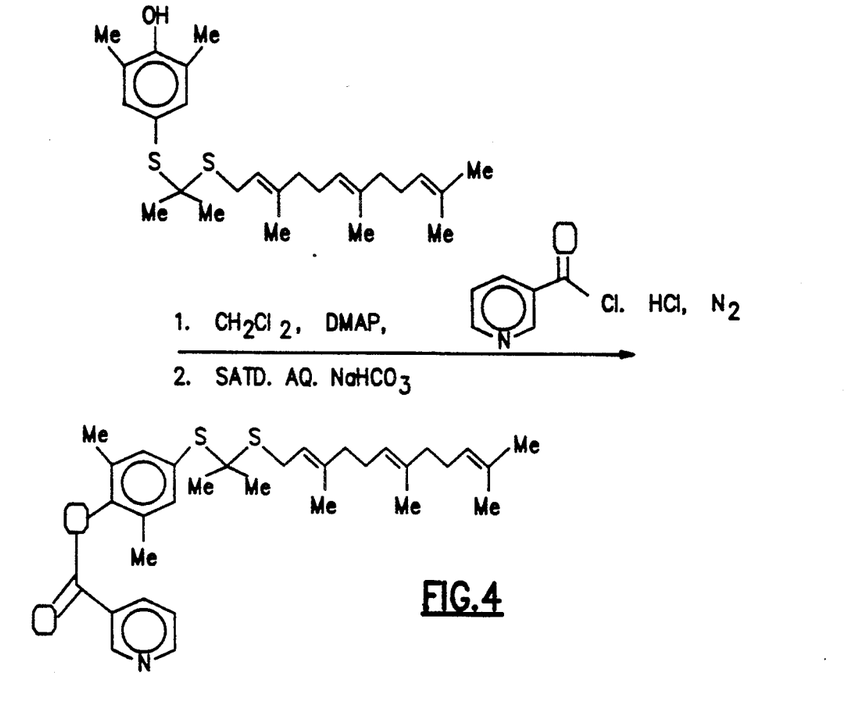
FIG. 4 shows the schematic procedure for preparing the prodrug of an ester.

Procedure for preparing the prodrug of an ester, preferably the nicotinate ester, 2,6-dimethyl-4-[[1-methyl-1-[(3,7,11-trimethyl-2,6,10-dodecatrienyl)thio]ethyl]thio]phenyl 3-pyridinecarboxylate To a solution of 2,6-Dimethyl-4[[1-methyl-1-[(3,7,11-trimethyl-2,6,10-dodecatrienyl)thio]ethyl]thio]phenol (2.0 g, 4.6 mmol) in 100 ml of dry dichloromethane, stirring under nitrogen and cooling in an ice water bath was added 1.7 g (13.9 mmol) of 4-dimethylaminapyridine. The resulting solution was then treated with 0.91 g (5.1 mmol) of nicotinoyl chloride, added as a solid which slowly dissolved as the reaction progressed. After 30 minutes the bath was removed and the mixture stirred for 1.5 hours at ambient temperature; 100 ml of saturated aqueous sodium bicarbonate solution was then added. After stirring vigorously for several minutes the mixture was poured into a separatory funnel and the phases separated. The dichloromethane phase was washed with 2×50 ml of distilled water and then 50 ml of brine before drying over stirred sodium sulfate. The latter was filtered off and the filtrate concentrated in vacuo; the residue was taken up in ethyl acetate and impregnated on silica gel by removal of solvent in vacuo. Flash column chromatography on silica gel and elution with 7:1/hexanes and then 4:1/ hexanes: EtOAc afforded 2.41 g (97.6 to yield of a clear, straw-colored oil. FIG. 4 shows the schematic procedure for preparing the prodrug of an ester.

MS (CI): m/e=537 (M+);

IR (KBr) $\nu_{max}$: 2964 (m), 2922 (m), 2856 (m), 1744 (s), 1420 (m), 1274 (s), 1172 (s), 1110 (s), 734 (m);

$^1$H NMR (CDCl$_3$) δ: 9.37 (1H, d, J=1.63 Hz), 8.81 (1H, dd, J=1.7, 4.8 Hz), 8.40 (1H, dt, J=1.9, 6.9 Hz), 7.42 (1H, ddd, J=0.7, 4.8, 5.5 Hz), 7.28 (1H, s), 5.24 (1H, dd, J=7.8 Hz), 2.12 (6H, s), 2.08–1.86 (8H, m), 1.67 (3H, s) 1.60 (3H, d, J=0.5 Hz), 1.52 (12H, s);

$^{13}$C NMR (CDCl$_3$) δ: 186.67, 162.83, 154.20, 151.38, 148.91, 139.57, 137.60, 137.13, 135.27, 131.27, 130.50, 129.95, 125.08, 124.37, 123.84, 123.60, 119.04, 57.98, 39.70, 39.61, 30.80, 28.42, 26.74, 26.36, 25.71, 21.70, 17.70, 16.39, 16.25, 16.04;

Anal. Calcd. for $C_{32}H_{43}NO_2S_2$: C, 71.46; H, 8.06; N, 2.60.
Found: C, 71.20; H, 7.95; N, 2.56.

EXAMPLE 40

Figure 5:
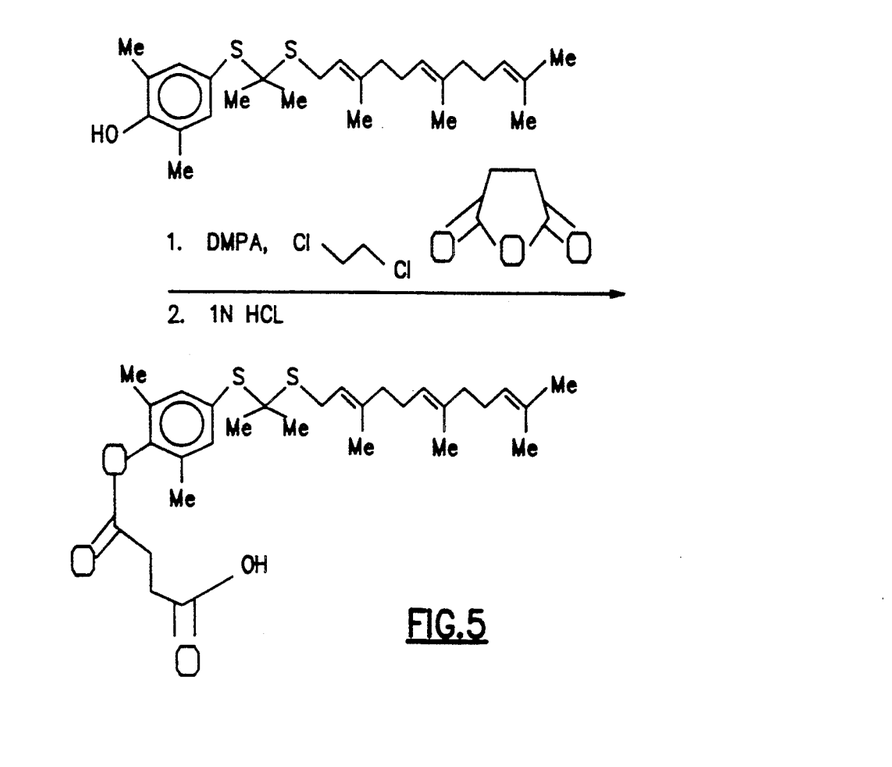
FIG. 5 shows the schematic procedure for preparing the prodrug of an ester.

Procedure for preparing the prodrug of an ester, preferably the succinate ester, 2,6-dimethyl-4-[[1-methyl-1-[(3,7,11 trimethyl-2,6,10-Dodecatrienyl)thio]ethyl]thio]phenyl butanedioate To a solution of 2,6-Dimethyl-4[[1-methyl-1-[(3,7,11-trimethyl-2,6,10-dodecatrienyl) thio]ethyl]thio]phenol (0.51 g, 1.2 mmol) in 25 ml of 1,2-dichloroethane was added 0.37 g (3.0 mmol) of 4-dimethylaminopyridine, followed by 0.15 g (1.5 mmol) of succinc anhydride. After stirring the solution overnight at room temperature under nitrogen, 25 ml of 1N HCl was added, and the mixture stirred vigorously for several minutes. The mixture was then poured into a separatory funnel, the phases separated, and the organic phase washed with another 25 ml of 1N HCl, then 25 ml of distilled water and finally 25 ml of brine. After drying over sodium sulfate, filtration and concentration of the filtrate in vacuo afforded the crude product as a gum. This material was impregnated on silica gel and then flash column chromatographed on silica gel, using 4:1/hexanes:EtOAC to elute less polar contaminants. Elution with 4:1/hexanes: EtOAC containing HOAC (0.5 ml/350 ml) caused the desired product to elute; fractions containing this material were combined and concentrated in vacuo to afford 222 mg of nearly colorless gum (34.7% yield). FIG. 5 shows the schematic procedure for preparing the prodrug of an ester.

MS (CI): m/e=279 for [Me$_2$CS(C$_{15}$H$_{25}$)]$^+$;

IR (KBr) $\nu_{max}$: 2964 (br. s), 2922 (br. s), 1760 (s), 1716 (s), 1176 (s), 1143 (s), 1108 (m);

$^1$H NMR (CDCl$_3$) δ: 7.19 (2H, s), 5.23 (1H, t, J=6.8 Hz), 5.01 (2H,br. m), 3.37 (2H, d, J=7.78 Hz), 2.86 (2H, dd, J=5.3, 7.67 Hz), 2.75 (2H, dd, J=5.3, 7.7 Hz), 2.06 (6H, s), 2.05-185 (8H, m), 1.66 (3H, d, J=0.7 Hz), 1.61 (3H, d, J=0.6 Hz), 1.53 (6H, s), 1.49 (6H, s);

$^{13}$C NMR (CDCl$_3$) δ: 177.86, 169.76, 148.99, 139.54, 136.99, 135.25, 131.27, 130.43, 129.50, 124.36, 123.82, 119.01, 95.80, 57.82, 39.68, 39.58, 30.74, 28.76, 28.44, 28.36, 26.71, 26.33, 25.69, 17.69, 16.22, 16.01;

Anal Calcd. for C$_{30}$H$_{44}$O$_4$S$_2$: C, 67.63; H, 8.32. Found: C, 67.65; H, 8.28.

We claim:

1. A compound of the formula wherein

R$^1$ represents C$_1$ to C$_6$ alkyl, hydroxy, hydrogen, or halogen;

R$^2$, R$^3$, R$^4$, and R$^5$ are identical or different and independently of one another are each hydrogen, C$_1$ to C$_6$ alkyl, phenyl, carboxylic acid esters, amides, and nitriles;

R$^6$, and R$^7$ are identical or different and independently of one another are each hydrogen, C$_1$ to C$_6$ alkyl, cyclic alkyls, chloroalkyls, fluoroalkyls, or COOR, wherein R is methyl or ethyl;

m is 0-2; and n is 1-3;

or a nontoxic pharmaceutically acceptable salt, hydrate, solvate or quaternary ammonium salt thereof.

2. The compound of claim 1 which is propanoic Acid, 2-[(4-hydroxy-3,5-dimethylphenyl)thio]-2-[(3,7,11-trimethyl-2,6,10-dodecatrienyl)thio]methyl ester.

3. The compound of claim 1 which is propanoic Acid, 2-[(4-hydroxy-3,5-dimethylphenyl)thio]-2-[(3,7,11-trimethyl-2,6,10-dodecatrienyl)thio]ethyl ester.

4. The compound of claim 1 which is propanoic Acid, 2-[(4-hydroxy-3,5-dimethyl phenyl)thio]-2-[(3,7,11,15-tetramethyl-2,6,10,14-hexadecatetraenyl)thio]ethyl ester.

5. The compound of claim 1 which is propanoic Acid, 2-[(4-hydroxy-3,5-dimethyl phenyl)thio]-2-[(3,7,11,15-tetramethyl-2,6,10,14-hexadecatetraenyl)thio]methyl ester.

6. The compound of claim 1 which is 5-[[1-methyl-1-[(3,7,11-trimethyl-2,6,10-dodecatrienyl) thio]ethyl]mercapto-2-hydroxybenzoic acid methyl ester.

7. A pharmaceutical composition comprising an effective amount of a compound of claim 1 and a pharmacologically acceptable carrier.

* * * * *